United States Patent [19]

Deguchi et al.

[11] Patent Number: 5,230,835
[45] Date of Patent: Jul. 27, 1993

[54] MILD NON-IRRITATING ALKYL GLYCOSIDE BASED DETERGENT COMPOSITIONS

[75] Inventors: Katsuhiko Deguchi; Kozo Saito; Hiroyuki Saijo, all of Tochigi, Japan

[73] Assignee: Kao Corporation, Tokyo, Japan

[21] Appl. No.: 762,180

[22] Filed: Sep. 20, 1991

Related U.S. Application Data

[63] Continuation of Ser. No. 387,769, Aug. 1, 1989, abandoned.

[30] Foreign Application Priority Data

| Aug. 4, 1988 | [JP] | Japan | 63-194871 |
| Aug. 29, 1988 | [JP] | Japan | 63-214140 |
| Sep. 2, 1988 | [JP] | Japan | 63-219877 |
| Nov. 1, 1988 | [JP] | Japan | 63-274353 |

[51] Int. Cl.$^5$ ............ C11D 1/12; C11D 1/83; C11D 1/66
[52] U.S. Cl. ............ 252/550; 252/174.17; 252/174.18; 252/174.21; 252/174.22; 252/DIG. 5
[58] Field of Search ............ 252/174.17, 174.18, 252/174.21, 174.22, DIG. 5, 550

[56] References Cited

U.S. PATENT DOCUMENTS

| 3,337,463 | 8/1967 | Schmolka et al. | 252/89 |
| 4,048,123 | 9/1977 | Hramchenko et al. | 252/545 |
| 4,147,652 | 4/1979 | Kaniecki | 252/156 |
| 4,240,921 | 12/1980 | Kaniecki | 252/156 |
| 4,490,279 | 12/1984 | Schmolka | 252/357 |
| 4,668,422 | 5/1987 | Malik | 252/174.17 |
| 4,678,606 | 7/1987 | Akhter et al. | 252/542 |
| 4,708,813 | 11/1987 | Snyder | 252/90 |
| 4,732,704 | 3/1988 | Biermann et al. | 252/547 |
| 4,758,376 | 7/1988 | Hirota et al. | 252/545 |

FOREIGN PATENT DOCUMENTS

| 0070075 | 7/1981 | European Pat. Off. | 252/174.17 |
| 0037161 | 10/1981 | European Pat. Off. | 232/174.21 |
| 0070074 | 1/1983 | European Pat. Off. | 252/174.1 |
| 0070076 | 1/1983 | European Pat. Off. | 252/549 |
| 0070077 | 1/1983 | European Pat. Off. | 252/174.17 |
| 0075995 | 4/1983 | European Pat. Off. | 252/174.17 |
| 0106692 | 4/1984 | European Pat. Off. | 252/174.17 |
| 0221774 | 5/1987 | European Pat. Off. | 252/547 |
| 0299654 | 1/1989 | European Pat. Off. | 252/174.17 |
| 6469695 | 3/1989 | Japan . | |
| 2205578 | 12/1986 | United Kingdom | 252/174.17 |
| 2181152 | 4/1987 | United Kingdom | 252/174.17 |
| 2185992 | 8/1987 | United Kingdom | 252/547 |
| WO87/02051 | 4/1987 | World Int. Prop. O. | 252/174.17 |
| 8809369 | 5/1988 | World Int. Prop. O. | 252/174.17 |

OTHER PUBLICATIONS

Grant & Hackh's Chemical Dictionary, ed. Roger Grant & Claire Grant, (5th ed.), p. 564.
CA113(8):61796n, "Detergents containing alkyl glycosides alkoxylated polyols or their sulfates or phosphates", Deguchi et al., Feb. 7, 1990.

Primary Examiner—Paul Lieberman
Assistant Examiner—Kery A. Fries
Attorney, Agent, or Firm—Birch, Stewart, Kolasch & Birch

[57] ABSTRACT

A detergent composition comprising the components (a) and (b) specified below in a (b)/(a) weight ratio within the range of 1/300 to ½, and a detergent composition comprising the components (a) and (c) specified below in a (c)/(a) weight ratio within the range of 1/300 to ½:

(a) An alkyl glycoside;
(b) A polyhydric alcohol-polyalkylene oxide adduct having an average molecular weight of 300 to 4,000 provided that when the polyhydric alcohol is ethylene glycol, the alkylene oxide is propylene oxide;
(c) A sulfate ester salt and/or a phosphate ester salt of a polyhydric alcohol-polyalkylene oxide adduct having an average molecular weight of 400 to 10,000.

The detergent composition according to the invention may further contain a nitrogen-containing surfactant as component (d).

15 Claims, No Drawings

MILD NON-IRRITATING ALKYL GLYCOSIDE BASED DETERGENT COMPOSITIONS

This application is a continuation of application Ser. No. 07/387,769 filed on Aug. 1, 1989 now abandoned.

FIELD OF THE INVENTION

The present invention relates to a detergent composition. More particularly, the present invention relates to a detergent composition having a much decreased irritancy and injuriousness to skin and hair, a high foaming power and detergency, a good removability upon rinsing and a good feel to the users' hands.

BACKGROUND OF THE INVENTION

Nowadays, the concern about material safety or non-hazardousness is growing and, in the field of detergents, various attempts have been made to moderate the dermatological actions of detergent compositions which come into contact with the human skin on numerous occasions, for example detergent compositions for washing clothing, kitchen utensils, housing equipment, human hair and body, etc. Thus, for instance, it has been proposed that such compositions should be adjusted to pH 5 to 6 (weak acidity) for bringing their pH closer to that of human skin and thereby rendering their action mild to the skin, or that detergent base materials as low in irritancy as possible should be used as the main detergent base ingredients. Known low-irritancy detergent bases include, for example, amino acid derivative surfactants and alkylphosphoric surfactants (cf. JP-B-50-40125, JP-B-51-42603, JP-B-55-9033 and JP-B-58-27319) (the term "JP-B" as used herein means an "examined Japanese patent publication"). However, these surfactants are disadvantageous in, for example, that when used alone, they cannot always develop their foaming power or detergency to a satisfactory extent or that their solubility is poor, although they are less irritating. In the case of detergent compositions for use in the kitchen, sodium alkylbenzenesulfonates are in wide use as base detergents having high detergency but they have drawbacks, namely, they potently cause removal of fat from the skin, tending to make the users' hands rough.

Therefore, it is a recent trend to use sodium alkylethoxysulfates, which are less irritating to the skin, as basic detergent ingredients in detergent compositions for washing kitchen utensils. Furthermore, the combined use of such auxiliary detergents as tertiary amine oxides or higher fatty acid diethanolamides has been found to produce further improvements in performance characteristics and at the same time render the action of the resulting detergent compositions to the skin milder. For instance, liquid detergent compositions containing an ethoxylated alkyl sulfate and a sulfate of an adduct of polyalkylene oxide with a neopentyl glycol or a polyhydric alcohol are described in JP-A-62-89797 (the term "JP-A" as used herein means an "unexamined Japanese patent application") (corresponding to GB 2 181 152 A), and liquid detergent compositions containing an anionic surfactant, an alkyl tertiary amino oxide, a higher fatty acid alkanolamide and a polypropylene oxide adduct of a polyhydric alcohols are described in JP-A-63-277300 (corresponding to GB 2 205 578 A).

However, under existing circumstances, the action of various detergent compositions to the skin is not yet at a satisfactorily low level although said action is much milder when compared with older detergent compositions.

On the other hand, alkyl glycosides, which are sugar-derived surfactants, are low-irritancy surfactants and it is known that, in spite of their being nonionic surfactants, they by themselves can form stable foam bubbles and, in addition, can serve as foam stabilizers for anionic surfactants. Accordingly, they have currently become a focus of attention. Thus, for instance, foaming surfactant compositions containing an alkyl glycoside and an anionic surfactant are described in JA-P-58-104625 (corresponding to U.S. Pat. No. 4,565,647), liquid detergent compositions for dishwashing with hands which contain an alkyl glycoside, an anionic surfactant and a fatty acid alkanolamide and have high foaming power and detergency together with low irritancy are described in JP-A-62-74999 (corresponding to U.S. Pat. No. 4,732,704) and forming compositions containing an alkyl glycoside, an anionic surfactant and an amine oxide or a fatty acid alkanol amide are described in JP-A-58-186429 (corresponding to U.S. Pat. No. 4,599,188).

However, the performance characteristics of these detergent compositions, though better than those of detergent compositions containing a polyoxyethylene alkyl ether sulfates as a main component, are not yet fully satisfactory. In particular, they have problems in that they are inferior in rinsing property after washing and in feel to hands.

SUMMARY OF THE INVENTION

Under these circumstances, the present inventors made intensive investigations in an attempt to draw out the characteristic features of alkyl glycosides as much as possible and, as a result, found that the combined use therewith of a polyhydric alcohol-polyalkylene oxide adduct or a polyhydric alcohol-polyalkylene oxide adduct-derived sulfate ester salt and/or phosphate ester salt results in much reduced dermal irritancy, in increased foaming power and detergency and in improvements in removability upon rinsing and feel to hands. These findings have now led to completion of the present invention.

Thus, the invention provides a detergent composition comprising the components (a) and (b) specified below in a (b)/(a) weight ratio within the range of 1/300 to $\frac{1}{2}$, and a detergent composition comprising the components (a) and (c) specified below in a (c)/(a) weight ratio within the range of 1/300 to $\frac{1}{2}$:

(a) An alkyl glycoside;
(b) A polyhydric alcohol-polyalkylene oxide adduct having an average molecular weight of 300 to 4,000 provided that when the polyhydric alcohol is ethylene glycol, the alkylene oxide is propylene oxide;
(c) A sulfate ester salt and/or a phosphate ester salt of a polyhydric alcohol-polyalkylene oxide adduct having an average molecular weight of 400 to 10,000.

The detergent composition according to the invention may further contain a nitrogen-containing surfactant as component (d).

DETAILED DESCRIPTION OF THE INVENTION

In the detergent composition according to the invention, the alkyl glycoside, namely component (a), is used as a main surfactant component and preferably has the general formula $$R^1(OR^2)_x G_y \quad (I)$$

wherein $R^1$ is a straight or branched alkyl or alkenyl group containing 8 to 18 carbon atoms or an alkylphenyl group in which the alkyl moiety may be straight or branched and contains 8 to 18 carbon atoms, $R^2$ is an alkylene group containing 2 to 4 carbon atoms, G is a reducing sugar-derived residue containing 5 or 6 carbon atoms, x indicates a mean value and is a number equal to 0 to 5, y indicates a mean value and is a number equal to 1 to 10.

In the above formula, $R^1$ is a straight or branched alkyl or alkenyl group containing 8 to 18 carbon atoms or an alkylphenyl group in which the alkyl moiety may be straight or branched and contains 8 to 18 carbon atoms. From the solubility, foaming power and detergency viewpoints, however, it is particularly preferable that the alkyl or alkenyl group or the alkyl moiety contains 10 to 14 carbon atoms.

While $R^2$ is an alkylene group containing 2 to 4 carbon atoms, an alkylene group containing 2 or 3 carbon atoms is particularly preferred from the water solubility viewpoint.

G is a residue derived from a reducing sugar containing 5 or 6 carbon atoms, the structure of the residue being determined by the mono- or oligosaccharide used as the starting material. Examples of the starting material for G include such monosaccharides as glucose, galactose, xylose, mannose, lyxose, arabinose and mixtures of these and such oligosaccharides as maltose, xylobiose, isomaltose, cellobiose, gentiobiose, lactose, sucrose, nigerose, turanose, raffinose, gentianose, melezitose and mixtures of these. Preferred from the availability and cost viewpoints are glucose and fructose among the monosaccharides and, among the oligosaccharides, maltose and sucrose. Among these mono- or oligosaccharides, glucose is particularly preferred.

The mean value x is equal to 0 to 5. Particularly preferred is a value of x which is equal to 0 to 2. This value is of significant in adjusting the water solubility and crystallinity of component (a). There is a tendency toward higher water solubility and lower crystallinity with the increasing value of x.

The mean value y is equal to 1 to 10. Particularly preferred is a value of x within the range of about 1.0 to 3.0. This value is desirable for the foaming intensifying components (b) or (c), which are to be described later herein in further detail, to produce their foaming intensifying to a satisfactory extent at lower addition levels.

In cases where the mean value y is greater than 1, i.e., where the alkyl glycoside of general formula (I) contains an alkyl glycoside having a disaccharide and/or further oligosaccharide chain as the hydrophilic group, the type of sugar chain bonding may be 1-2, 1-3, 1-4 or 1-6, $\alpha$- or $\beta$-pyranoside or furanoside bonding or a mixed bonding type including these materials. The sugar chain length, i.e., the value y, can be measured or determined by the proton NMR method.

The component (a) of the present invention may be used either singly or in the form of a mixture of two or more.

Generally, the detergent composition according to the present invention contains the component (a) in an amount of 1 to 60% by weight (hereinafter, unless otherwise indicated, all "%" are by weight), preferably 10 to 40%.

The component (b) in the composition according to the invention is a polyhydric alcohol-polyalkylene oxide adduct provided that when the poly-hydric alcohol is ethylene glycol, the alkylene oxide is propylene oxide.

Preferred example of the polyhydric alcohol, which is the starting material for component (b) include dihydric alcohols such as ethylene glycol, propylene glycol and neopentyl glycol; tri- and further polyhydric alcohols such as glycerol, poly-glycerol trimethylolpropane, pentaerythritol and sorbitol. Particularly preferred among the polyalkylene oxide adducts derived from such polyhydric alcohols are ethylene glycol- or glycerol-polypropylene oxide adducts. These compounds may be used either singly or in the form of a mixture of two or more of them as component (b).

The component (b), when incorporated in the alkyl glycoside-containing detergent composition, serves to further reduce the dermal irritancy thereof and, in addition, increases the detergency and foaming power and improves the rinsing property and feel to hands when using the composition.

For the development of these effects, the polyhydric alcohol-polyalkylene oxide adduct should have a molecular weight within the range of 300 to 4,000, preferably 500 to 2,000. When the molecular weight is outside the range, the irritancy-reducing effect and detergency- and foaming power-increasing effect will be much less; the rinsing property or feel to the users' hands will not be improved to a substantial extent.

The detergent composition according to the invention should preferably contain the component (b) in an amount of 0.1 to 10%, more preferably 1 to 5%. At an level below 0.1%, the effects of the invention will not be produced while, at a level of above 10%, the stability of said composition will be unfavorably decreased.

In the detergent composition according to the invention, the (b)/(a) weight ratio should be 1/300 to ½, preferably 1/200 to 2/5, more preferably 1/100 to ⅓.

The component (c) in the composition according to the invention is a polyhydric alcohol-polyalkylene oxide adduct sulfate ester salt and/or phosphate ester salt.

Preferred examples of the polyhydric alcohol which serves as the starting material for component (c) are dihydric alcohols such as ethylene glycol, propylene glycol and neopentyl glycol; and trihydric and polyhydric alcohols such as glycerol, polyglycerol, trimethylolpropane, pentaerythritol and sorbitol. The polyalkylene oxide is preferably an addition polymer of either one or both of ethylene oxide (EO) and propylene oxide (PO). When it is a coaddition polymer of PO and EO, it may be a block copolymer or a random copolymer. The average molecular weight of the polyhydric alcohol-polyalkylene oxide adduct should be within the range of 400 to 10,000, preferably within the range of 800 to 6000. If the molecular weight is outside the above range, the effects of the invention will not be produced.

The polyhydric alcohol-polyalkylene oxide adduct sulfate ester salt and/or phosphate ester salt can be produced in the conventional manner (cf. e.g., JP-A-57-5796). The salt is a water-soluble salt and preferably is an alkali melt salt, alkaline earth metal salt, alkanolamine salt or ammonium salt, for instance. Among them, alkali metal salts and alkaline earth metal salts are particularly preferred. These components (c) may be used either singly or in the form of a mixture of two or more of them. While the sulfate ester salt and/or phosphate ester salt can have a number of sulfate and/or phosphate groups which corresponds to the available valence of the polyhydric alcohol, it is preferable that each molecule should have 1 to 4 sulfate and/or phosphate groups.

Among these polyhydric alcohol-polyalkylene oxide adduct sulfate ester salt and/or phosphate ester salt, ethylene glycol, propylene glycol or glycerol with polyethylene oxide adduct sulfate ester salt are particularly preferred.

The detergent composition according to the invention should preferably contain the component (c) in an amount of 0.1 to 10%, more preferably 1 to 5%. At an addition level below 0.1%, the effects of the invention will not be produced while, at a level above 10%, the stability of the composition will be unfavorably decreased.

In the detergent composition according to the invention, the (c)/(a) weight ratio should be within the range of 1/300 to ½, preferably 1/200 to 2/5, more preferably 1/300 to ⅓.

With regard to the nitrogen-containing surfactant, namely component (d), it is preferable to use one or more of the tertiary amino oxides, sulfobetaines, carbobetaines, and amide type surfactants. Preferred examples of these nitrogen-containing surfactants include the compounds (1) to (4) as described below.

(1) Amine Oxides of Formula (II):

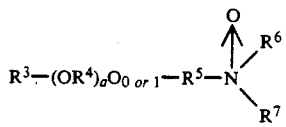

wherein $R^3$ represents a straight or branched alkyl or alkylamido group containing 8 to 18 carbon atoms, $R^4$ represents an alkylene group containing 2 or 3 carbon atoms, a represents an integer of 0 to 30, $R^5$ represents an alkylene group containing 0 to 5 carbon atoms, and $R^6$ and $R^7$, which may be the same or different, each represents a member selected from the group consisting of an alkyl group containing 1 to 3 carbon atoms, an alkanol group containing 1 to 3 carbon atoms, a group of the formula $-(C_2H_4O)_{1-6}H$ and mixtures thereof.

(2) Sulfobetaines of Formula (III):

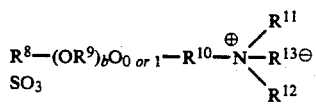

wherein $R^8$ represents a straight or branched alkyl or alkylamido group containing 8 to 18 carbon atoms, R9 represents an alkylene group containing 2 or 3 carbon atoms, b represents an integer of 0 to 30, $R^{10}$ is an alkylene group containing 0 to 5 carbon atoms, $R^{11}$ and $R^{12}$, which may be the same or different, each represents a group selected from the member consisting of an alkyl group containing 1 to 3 carbon atoms, an alkanol group containing 1 to 3 carbon atoms, a group of the formula $-(C_2H_4O)_{1-6}H$ and mixtures thereof and $R^{13}$ represents an OH-containing or OH-free alkylene group containing 2 to 5 carbon atoms.

(3) Carbobetaines of Formula (IV):

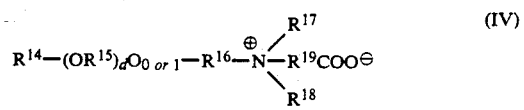

wherein $R^{14}$ represents a straight or branched alkyl or alkyl-amido group containing 8 to 18 carbon atoms, $R^{15}$ represents an alkylene group containing 2 or 3 carbon atoms, d represents an integer of 0 to 30, $R^{16}$ represents an alkylene group containing 0 to 5 carbon atoms, $R^{17}$ and $R^{18}$, which may be the same or different, each represents a group selected from the group consisting of an alkyl group containing 1 to 3 carbon atoms, an alkanol member containing 1 to 3 carbon atoms, a group of the formula $-(C_2H_4O)_{1-6}H$ and mixtures thereof, and $R^{19}$ represents an OH-containing or OH-free alkylene group containing 1 to 5 carbon atoms.

(4) Amide Type Surfactants represented by Formulae (V) to (IX);

(4-1) Formula (V):

wherein $R^{20}$ is a straight or branched alkyl group containing 7 to 19 carbon atoms, and $R^{21}$ and $R^{22}$ which may be the same or different, each represents a member selected from the group consisting of a hydrogen atom, an alkyl group containing 1 to 3 carbon atoms, an alkanol group containing 1 to 3 carbon atoms, a group of the formula $-(C_2H_4O)_{1-4}H$ and mixtures thereof;

(4-2) Formula (VI):

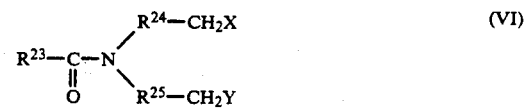

wherein $R^{23}$ represents a straight or branched alkyl group containing 7 to 19 carbon atoms, $R^{24}$ and $R^{25}$ each represents an alkylene group containing 0 to 4 carbon atoms and X and Y, which may be the same or different, each represents a hydrogen atoms, the group OH or the group $-COOM^1$ or $-SO_3M^2$ ($M^1$ and $M^2$ each represents a hydrogen atom, an alkali or alkaline earth metal or an alkanolamine-derived ammonium (group);

(4-3) Formulae (VII to IX):

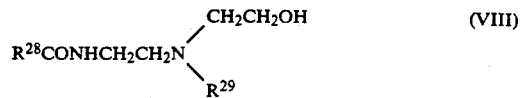

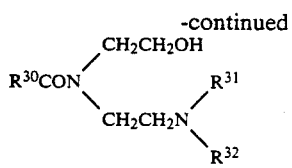

wherein $R^{26}$, $R^{28}$ and $R^{30}$, each represents a straight or branched alkyl or alkenyl group containing 7 to 19 carbon atoms, $R^{27}$ represents a hydrogen atom or a group of the formula —$(CH_2CH_2O)_mH$ in which m represents an integer of 5 to 20, $R^{29}$ and $R^{31}$ each represents a group of the formula —$CH_2COOM$ or —$CH_2CH_2COOM$ in which M is a hydrogen or alkali metal atom or an alkanolamine-derived ammonium group, $R^{32}$ is a hydrogen atom or a group of the formula —$CH_2COOM$ or —$CH_2CH_2COOM$ in which M is as defined above.

Among the amide type surfactants represented by formulae (V) and (VII), a fatty acid alkanol amide or polyoxyethylene adduct thereof are particularly preferred.

Among the amide type surfactants represented by formulae (VI), (VIII) and (IX), the surfactants which are classified as an amideamino acid amphoteric surfactant are particularly preferred.

Preferred specific examples of the amideamino acid amphoteric surfactants of formula (VIII) include N-lauroyl-N'-carboxymethyl-N'-(2-hydroxyethyl)ethylenediamine, N-lauroyl-N'-carboxyethyl-N'-(2-hydroxyethyl) ethylenediamine, N-myristoyl-N'-carboxymethyl-N'-(2-hydroxyethyl)ethylenediamine, N-myristoyl-N'-carboxyethyl-N'-(2-hydroxyethyl)ethylenediamine, N-palmitoyl-N'-carboxymethyl- N'(2-hydroxyethyl)ethylenediamine, N-palmitoyl-N'-carboxyethyl-N'-(2-hydroxyethyl)ethylenediamine, and salts thereof. Among them, compounds having a straight alkyl group having 9 to 13 carbon atoms, as $R^{28}$, are particularly preferred.

Preferred specific examples of the amideamino acid ampholytic surfactants of formula (IX) include N-lauroyl-N-(2-hydroxyethyl)-N'-carboxymethylethylenediamine, N-lauroyl-N-(2-hydroxyethyl)-N',N'-bis (carboxymethyl)ethylenediamine, N-lauroyl-N-(2-hydroxyethyl)-N',N'-bis(carboxyethyl)ethylenediamine, N-myristoyl-N-(2-hydroxyethyl)-N'-carboxymethyl)ethylenediamine, N-myristoyl-N-(2-hydroxyethyl)-N',N'-bis(carboxymethyl)ethylenediamine, N-myristoyl-N-(2-hydroxyethyl)-N',N'-bis(carboxyethyl)ethylenediamine, N-palmitoyl-N-(2-hydroxyethyl)-N'-carboxymethylethylenediamine, N-palmitoyl-N-(2-hydroxyethyl)-N,N'-bis(carboxymethyl)ethylenediamine, N-palmitoyl-N-(2-hydroxyethyl)-N',N'-bis(carboxyethyl)ethylenediamine, and salts thereof. Among them, compounds having a straight alkyl group having 11 to 13 carbon atoms, as $R^{30}$, are particularly preferred.

Specific examples of the salts include alkali metal salts such as sodium salt, alkaline earth metal salts such as magnesium salt, alkanolamine salts such as triethanolamine salt, and further, ammonium salts. These salts often contain inorganic salts as contaminants. Therefore, it is preferable to use desalted amideamino acid type amphoteric surfactants prepared by eliminating a part or the whole of such contaminant inorganic salts.

These compounds may be used either singly or in an admixture of two or more of them as component (d).

When added to detergent compositions comprising an alkyl glycoside, namely the component (a), the component (d) produces the following effects: further reduction in skin irritancy, increase in detergency and in foaming capacity, and improvement in rinsing property and in feel to users' hands.

For the development of such effects, the component (d) should preferably be contained in the composition according to the present invention in an amount of 0.1 to 10%, more preferably 1 to 5%.

In the detergent composition according to the present invention, the (d)/(a) weight ratio should be within the range of 1/300 to ½, preferably 1/200 to 2/5, more preferably 1/100 to ⅓.

The detergent composition according to the present invention may contain, in addition to the above-mentioned components, any of other known surfactants suited for use in detergent compositions, if necessary, for the purpose of increasing the detergency and/or foaming power, at an adequate addition level. Such surfactants are, for example, nonionic surfactants such as polyoxyethylene (average number of moles of EO added = 4 to 20)-alkyl ($C_7$ to $C_{18}$, straight Or branched) ethers; and anionic surfactants much as α-olefin ($C_8$ to $C_{20}$)- sulfonic acid salts (Na, K, Mg, triethanolamine (TEA) or $NH_4$ salts), polyoxyethylene (average number of moles of EO added = 2 to 8)-alkyl ($c_8$ to $C_{18}$, straight or branched) sulfate ester salts (Na, K, Mg, TEA or $NH_4$ salts), α-sulfotatty acid ester salts

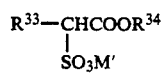

in which $R^{33} = C_{8-18}$, $R^{34} = C_{1-4}$, M' = alkali metal), monoalkyl ($C_8$ to $C_{18}$) phosphate salts (Na, K, TEA or arginine salts), and straight alkyl ($C_{10}$ to $C_{18}$)-benzenesulfonic acid salts (Na, K or Mg salts).

The detergent composition according to the present invention as such should preferably have a pH within the range of 4 to 10, more preferably a pH of 5 to 8.

The detergent composition according to the invention may further contain any other ingredients each at an addition level at which the phase separation stability, detergent performance and foaming capacity of the composition will not be affected. Thus, for example, lower aliphatic alcohols such as ethyl alcohol, solubilizing agents such as sodium or potassium salt of toluene- or xylenesulfonic acid or urea, viscosity modifiers such as clay minerals and water-soluble high-molecular substances, water-insoluble abrasives such as calcite, silica, calcium phosphate, zeolite, polyethylene, nylon and polystyrene, humectants such as glycerin and sorbitol, feeling-improvers such as cationized cellulose, enzymes, perfumes, colorants, preservatives, antifungal agents and the like may be added to the composition.

The detergent composition according to the present invention is a low-irritancy detergent composition of high practical value which has excellent detergency and high foaming capacity and which is mild in action to skin and hair, less able to make hands rough, and excellent in removability upon rinsing and in feel to hands.

The following examples illustrate the present invention in further detail. It is to be noted, however, that they are by no means limitative of the scope of the invention. Unless otherwise specified, all percents are by weight.

Testing Methods and Evaluation Criteria (1) Foaming Power Test

The foaming power is measured for the case where commercial butter is added as a dirt component at an addition level of 0.1% to a detergent solution having a detergent concentration of 0.5%. A 40-ml portion of the butter-added detergent solution is placed in a glass cylinder having a diameter of 5 cm and stirred by means of a rotating stirring device for 10 minutes. Immediately after stopping of the stirring, the height of the foam produced is measured.

(2) Detergency Test

Sudan III (red pigment) is added as an indicator at an addition level of 0.1% to beef tallow. A 2.5-gram portion of the mixture is spread on a porcelain plate (25 cm in diameter). Plates prepared in this way are washed by scrubbing with a sponge soaked with 3 g of the detergent composition and 27 g of water (hardness 3.5° DH) at 20° C. The detergency is expressed in terms of the number of plates washed until beef tallow cannot be removed completely from the plate any more.

(3) Rinsing Property Test 3 liters of the sample solution having a detergent concentration of 0.25% placed in a vat having a diameter of 30 cm and a height of 12 cm is stirred by means of a rotating stirrer for 10 minutes for foaming, then the cock at the bottom of the vat is opened for draining the liquid phase alone. Then, 3 liters of tap water is added to the vat and, after 10 minutes of stirring by means of a rotating stirrer, drained in the same manner. This draining procedure is repeated using fresh portions of tap water until no more foam is observed in the vat. The removability is evaluated in terms of the number of tap water exchanges.

(4) Feel to hands during use and after use

Two kinds of detergent compositions, A and B, are prepared. Each is dissolved in water in a 2-liter beaker to give an aqueous detergent solution having a concentration of 10% by weight. The aqueous solutions of the detergent compositions A and B are maintained at 40° C. and tested for their feel in the manner of comparative organoleptic examination as follows.

1) Feel of the liquid

The left and right hands are separately dipped into the aqueous solutions of detergents A and B to the wrist. After 1 minute of continued dipping, the feel of detergent B is compared with that of detergent A and scored according to the following criteria:

| | |
|---|---|
| Detergent B is less slimy | +2 |
| Detergent B is rather less slimy | +1 |
| Equivocal | ±0 |
| Detergent B is rather more slimy | −1 |
| Detergent B is more slimy | −2 |

2) Feel after Use

After thorough rinsing, the hands are wiped with a dry towel and the feel of detergent B to hands is compared with that of detergent A and scored in accordance with the following criteria:

| | |
|---|---|
| Detergent B is less sticky | +2 |
| Detergent B is rather less sticky | +1 |
| Equivocal | ±0 |
| Detergent B is rather more sticky | −1 |
| Detergent B is more sticky | −2 |

The above test is performed using 10 panelists and the feel of detergent B is evaluated in terms of the total score for each item.

(5) Hand Roughening Effect Test

A detergent solution containing 5% by weight of the test detergent composition is prepared. The hand is dipped in this solution maintained at 30° C. for 20 minutes everyday for consecutive 3 days. On the 4th day, the condition of the hand of each of 5 panelists is observed macroscopically according to the criteria shown below. The hand roughening effect is expressed in terms of the mean score.

In this test, it is desirable that the mean score should be not less than 4.

| | |
|---|---|
| Little hand roughening | 5 |
| Minimal hand roughening | 4 |
| Slight hand roughening | 3 |
| Moderate hand roughening | 2 |
| Marked hand roughening | 1 |

EXAMPLE 1

The compositions specified below in Table 1 were prepared and evaluated for detergency, foaming power, removability upon rinsing, feel to hands during use and after use, and hand roughening effect by the respective evaluation methods mentioned above. The results obtained are shown in Table 1.

In the comparative test for the feel to hands during use and after use, the detergent composition for comparison (composition No. 9 in Table 1) was the detergent A and the detergent compositions Nos. 1–8 in Table 1 each was the detergent B.

TABLE 1

| | Composition No. (weight percent) | | | | | | | | |
|---|---|---|---|---|---|---|---|---|---|
| | Product of the Invention | | | | | Comparative Product | | | |
| Component | 1 | 2 | 3 | 4 | 5 | 6 | 7 | 8 | 9 |
| Component (a) | | | | | | | | | |
| Alkylglycoside of general formula (I) (x = 0, G: glucose residue) | | | | | | | | | |
| $R^1$ / $y$ | | | | | | | | | |
| $C_9$-$C_{11}$ alkyl / 1.2 | 23 | 23 | 23 | | | | 23 | | 23 |
| $C_9$-$C_{11}$ alkyl / 1.7 | | | | 23 | 23 | 23 | | 23 | |
| Component (b) | | | | | | | | | |
| PPG100[*1] (diol type [*2]) | | | | | | 3 | | | |
| PPG1000[*1] (diol type[*2]) | 3 | | | | | | | | 0.05 |
| PPG2000[*1] (triol type[*3]) | | 3 | | | | | | | |
| PPG5000[*1] (triol type[*3]) | | | | | | | | 3 | |

TABLE 1-continued

| Component | Composition No. (weight percent) | | | | | | | | |
|---|---|---|---|---|---|---|---|---|---|
| | Product of the Invention | | | | | Comparative Product | | | |
| | 1 | 2 | 3 | 4 | 5 | 6 | 7 | 8 | 9 |
| Trimethylolpropane-EO adduct (1500*1) | | | 3 | | | | | | |
| Sorbitol-PO adduct (3000*1) | | | | 4 | | | | | |
| Pentaerythritol-PO adduct (4000*1) | | | | | 4 | | | | |
| PEG1500*1 | | | | | | 4 | | | |
| Water | Balance | Balance | Balance | Balance | Balance | Balance | Balance | Balance | Balance |
| Detergency (number of plates) | 7 | 7 | 7 | 7 | 7 | 4 | 4 | 4 | 4 |
| Foaming power (mm) | 92 | 91 | 90 | 91 | 91 | 30 | 24 | 32 | 15 |
| Rinsing property (times) | 5 | 5 | 5 | 5 | 5 | 8 | 8 | 8 | 8 |
| Feel to hands | | | | | | | | | |
| During use | +9 | +8 | +8 | +8 | +8 | +1 | +1 | +1 | ±0 |
| After use | +11 | +11 | +10 | +10 | +10 | +1 | +1 | +1 | ±0 |
| Ability to make hands rough | 4.8 | 4.8 | 4.7 | 4.8 | 4.7 | 3.2 | 3.5 | 3.1 | 3.0 |

*1The numerical value indicates the average molecular weight of the compound.
*2Ethylene glycol-PO adduct.
*3Glycerol-PO adduct.

EXAMPLE 2

| Shampoo (for hair or body): | (% by weight) |
|---|---|
| Alkyl glycoside of formula (I) [$x = 1$, $y = 1.5$, $R^1 = C_{10}$–$C_{13}$, $R^2 = C_2$, G = glucose residue] | 20 |
| PPG 2000 (diol type) | 2 |
| Cocofatty acid diethanolamide | 0.5 |
| Ethanol | 3 |
| Perfume | q.s. |
| Water | balance |
| | 100 |

(pH adjusted to 7.0)

EXMAPLE 3

| Bathroom detergent composition: | (% by weight) |
|---|---|
| Alkyl glycoside of general formula (I) [$x = 0$, $y = 2.3$, $R^1 = C_{10}$–$C_{14}$, (branched), G = glucose residue] | 20 |
| Pentaerythritol-PO adduct (molecular weight: 2,000) | 3 |
| Citric acid | 4 |
| Perfume, colorant | q.s. |
| Water | balance |
| | 100 |

(pH adjusted to 5.0)

EXAMPLE 4

| Liquid cleanser: | (% by weight) |
|---|---|
| Alkyl glycoside of general formula (I) [$x = 2$, $y = 1.1$, $R^1 = C_9$–$C_{11}$, $R^2 = C_2$, G = glucose residue] | 4 |
| Trimethylolpropane-EO adduct (molecular weight: 3,000) | 3 |
| Abrasive (silica) | 40 |
| Perfume, preservative | q.s. |
| Water | balance |
| | 100 |

(pH adjusted to 7.5)

EXAMPLE 5

The compositions specified below in Table 2 were prepared and evaluated for detergency, foaming power, removability upon rinsing, feel to hands during use and after use, and hand roughening effect by the respective evaluation methods mentioned above. The results obtained are shown in table 2.

In the comparative test for the feel to hands during use and that after use, the detergent composition for comparison (composition No. 17 in Table 2) was the detergent A and the detergent compositions Nos. 1–16 in Table 2 each was the detergent B.

TABLE 2

| Component | Composition No. (weight percent) | | | | | | | | |
|---|---|---|---|---|---|---|---|---|---|
| | Product of the Invention | | | | | | | | |
| | 1 | 2 | 3 | 4 | 5 | 6 | 7 | 8 | 9 |
| Component (a) Sugar derivative type surfactant of general formula (I) ($x = 0$, G: glucose residue) | | | | | | | | | |
| $R^1$ ... $y$ | | | | | | | | | |
| $C_9$–$C_{11}$ alkyl  1.1 | 23 | 23 | 23 | 23 | | | | 23 | 23 |
| $C_9$–$C_{11}$ alkyl  1.4 | | | | | 23 | 23 | 23 | | |
| Component (d) | | | | | | | | | |
| $C_{11}H_{23}CON(C_2H_4OH)_2$ | 3 | | | | | 3 | | 2 | 2 |
| $C_{12}H_{25}\overset{O}{\underset{\uparrow}{N}}(CH_3)_2$ | | | 3 | | | | | 2 | |

TABLE 2-continued

| Component | Composition No. (weight percent) | | | | | | | | |
|---|---|---|---|---|---|---|---|---|---|
| $CH_{14}H_{29}N^{\oplus}(CH_3)_2CH_2CHCH_2SO_3^{\ominus}$<br>$\phantom{XXXXXXXXXXXXX}OH$ | 3 | | | 3 | | | | 2 | |
| $C_{12}H_{25}N^{\oplus}(CH_3)_2CH_2COO^{\ominus}$ | | 3 | | | 3 | | | | |
| Component (b) | | | | | | | | | |
| PPG100*[1] (diol type*[2]) | | | | | | | | | |
| PPG1000*[1] (diol type*[2]) | 3 | 3 | 3 | 3 | | | | 2 | 2 |
| PPG2000*[1] (triol type*[3]) | | | | | 3 | | | | |
| PPG5000*[1] (triol type*[3]) | | | | | | | | | |
| Trimethylolpropane-EO adduct (1500*[1]) | | | | | | 3 | | | |
| Sorbitol-PO adduct (3000*[1]) | | | | | | | 3 | | |
| Water | Balance | Balance | Balance | Balance | Balance | Balance | Balance | Balance | Balance |
| Detergency (number of plates) | 8 | 8 | 8 | 8 | 8 | 8 | 8 | 8 | 8 |
| Foaming power (mm) | 94 | 96 | 96 | 94 | 93 | 94 | 93 | 96 | 96 |
| Rinsing property (times) | 5 | 5 | 5 | 5 | 5 | 5 | 5 | 5 | 5 |
| Feel to hands | | | | | | | | | |
| During use | +9 | +10 | +9 | +9 | +9 | +9 | +9 | +9 | +9 |
| After use | +11 | +11 | +11 | +11 | +11 | +11 | +11 | +11 | +11 |
| Ability to make hands rough | 4.8 | 4.8 | 4.8 | 4.8 | 4.7 | 4.7 | 4.7 | 4.8 | 4.8 |

| | Product of the Invention | | | | Comparative Product | | | |
|---|---|---|---|---|---|---|---|---|
| | 10 | 11 | 12 | 13 | 14 | 15 | 16 | 17 |
| Component (a) | | | | | | | | |
| Sugar derivative type surfactant of general formula (I) ($x = 0$, G: glucose residue) | | | | | | | | |
| $R^1$ / y | | | | | | | | |
| $C_9$–$C_{11}$ alkyl  1.1 | 23 | 23 | 23 | 23 | 23 | | | |
| $C_9$–$C_{11}$ alkyl  1.4 | | | | | | 23 | 23 | 23 |
| Component (d) | | | | | | | | |
| $C_{11}H_{23}CON(C_2H_4OH)_2$ | | | | 2 | | | | |
| $C_{12}H_{25}\overset{\uparrow O}{N}(CH_3)_2$ | 2 | 2 | 3 | | | 3 | | 0.05 |
| $CH_{14}H_{29}N^{\oplus}(CH_3)_2CH_2CHCH_2SO_3^{\ominus}$<br>$\phantom{XXXXXXXXXXXXX}OH$ | 2 | | | 3 | | | 3 | |
| $C_{12}H_{25}N^{\oplus}(CH_3)_2CH_2COO^{\ominus}$ | | 2 | | | | | | |
| Component (b) | | | | | | | | |
| PPG100*[1] (diol type*[2]) | | | | | 2 | | | |
| PPG1000*[1] (diol type*[2]) | 2 | 1 | 0.5 | | | | | |
| PPG2000*[1] (triol type*[3]) | | | | 8 | | | | |
| PPG5000*[1] (triol type*[3]) | | | | | | | 3 | |
| Trimethylolpropane-EO adduct (1500*[1]) | | 1 | | | | | | |
| Sorbitol-PO adduct (3000*[1]) | | | | | | | | 0.05 |
| Water | Balance | Balance | Balance | Balance | Balance | Balance | Balance | Balance |
| Detergency (number of plates) | 8 | 8 | 7 | 7 | 3 | 4 | 4 | 2 |
| Foaming power (mm) | 97 | 95 | 92 | 94 | 37 | 45 | 42 | 30 |
| Rinsing property (times) | 5 | 5 | 5 | 5 | 9 | 10 | 9 | 9 |
| Feel to hands | | | | | | | | |
| During use | +9 | +9 | +8 | +9 | +2 | +3 | +3 | ±0 |
| After use | +11 | +11 | +10 | +11 | +2 | +3 | +3 | ±0 |
| Ability to make hands rough | 4.8 | 4.7 | 4.7 | 4.5 | 3.1 | 2.9 | 4.0 | 3.9 |

Note to Table 2:
*[1]the numeral value indicates the average molecular weight of the compound.
*[2]Ethylene glycol-PO adduct.
*[3]Glycerol-PO adduct.

EXAMPLE 6

| Shampoo (for hair or body): | (% by weight) |
|---|---|
| Alkyl glycoside[1] | 20 |
| Amide type surfactant[2] | 3 |
| PPG 1000 (diol type) | 2 |
| Ethanol | 3 |
| Perfume | q.s. |
| Water | balance |// 
| | 100 |

(pH adjusted to 7.0)
[1]In general formula (I), $x = 1$, $y = 1.3$, $R^1 = C_{10}$–$C_{13}$, $R^2 = C_2$, G = glucose residue.

[2] $R-\overset{O}{\underset{\|}{C}}-\overset{CH_3}{\underset{|}{N}}-CH_2CH_2SO_3Na$ (R = cocofatty acid residue)

EXAMPLE 7

| Bathroom detergent composition: | (% by weight) |
|---|---|
| Alkyl glycoside[3] | 5 |
| Carbobetaine[4] | 0.5 |
| Pentaerythritol-EO adduct (molecular weight: 1,500) | 3 |
| Citric acid | 4 |
| Perfume | q.s. |
| Colorant | q.s. |
| Water | balance |
|  | 100 |

(pH adjusted to 5.0)
[3] In general formula (I), $x = 0$, $y = 2.3$, $R^1 = C_{10}-C_{14}$ (branched), G = glucose residue.

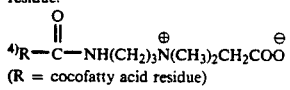

[4] $R-\overset{O}{\underset{\|}{C}}-NH(CH_2)_3\overset{\oplus}{N}(CH_3)_2CH_2\overset{\ominus}{COO}$ (R = cocofatty acid residue)

EXAMPLE 8

The liquid detergent compositions specified in Table 3 were prepared using various alkyl glycosides and various polyhydric alcohol-ethylene oxide (EO) or propylene oxide (PO) adduct sulfate ester salts or phosphate ester salts. They were evaluated for detergency, foaming power, rinsing property, feel to hands and hand roughening effect. The results obtained are shown in Table 3.

In the comparative test for the feel to hands during use and that after use, the detergent composition for comparison (composition No. 15 in Table 3) was the detergent A and the detergent compositions Nos. 1–14 in Table 3 each was the detergent B.

The abbreviations for components as used in the table should be interpreted as follows. For instance, GLY-EO-DS(Na) (1000) stands for glycerol-EO adduct (average molecular weight 1,000) disulfate ester salt (sodium salt).

Abbreviations for Polyhydric Alcohols

EGL: Ethylene glycol
PGL: Propylene glycol
GLY: Glycerol
TMP: Trimethylolpropane
PET: Pentaerythritol
SOR: Sorbitol
NPG: Neopentyl glycol

Abbreviations for Alkylene Oxides

EO: Ethylene oxide adduct
PO: Propylene oxide adduct

Abbreviations for Esters

MS: Monosulfate ester
DS: Disulfate ester
TS: Trisulfate ester
DS: Diphosphate ester
TP: Triphosphate ester

Abbreviations for Salts

Na: sodium salt
K: Potassium salt
TEA: Triethanolamine salt

TABLE 3

| Component | Composition No. (weight percent) |||||||||||||||
|---|---|---|---|---|---|---|---|---|---|---|---|---|---|---|---|
| | Product of the Invention |||||||| Product of the Invention ||| Comparative Product ||||
| | 1 | 2 | 3 | 4 | 5 | 6 | 7 | 8 | 9 | 10 | 11 | 12 | 13 | 14 | 15 |
| Component (a) | | | | | | | | | | | | | | | |
| General formula (I) | | | | | | | | | | | | | | | |
| $R^1$ / $R^2$ / x / y / G | | | | | | | | | | | | | | | |
| $C_8$–$C_{11}$ alkyl — 0 1.2 Glucose residue | 23 | 23 | | | 23 | 23 | 23 | 23 | | | | 23 | 23 | 23 | |
| $C_{10}$–$C_{13}$ alkyl — 0 1.7 Glucose residue | | | 23 | 23 | | | | | 23 | 23 | 23 | | | | 23 |
| Component (c) | | | | | | | | | | | | | | | |
| EGL—EO—DS (Na) (300) | | | | | | | | | 3 | | | | | | |
| EGL—EO—MS (Na) (700) | 3 | | | | | | | | | | | | | | |
| GLY—PO—DS (K) (1,500) | | 3 | | | | | | | | | | | | | |
| GLY—PO—DP (Na) (1,500) | | | 3 | | | | | | | | | | | | |
| PGL—EO—TS (Na) (6,000) | | | | 3 | | | | | | | | | | | |
| PGL—PO—TP (K) (4,000) | | | | | 3 | | | | | | | | | | |
| PET—EO—MS (TEA) (2,000) | | | | | | 2 | | | | | | | | | |
| PET—PO—DP (K) (2,000) | | | | | | | 3 | | | | | | | | |
| SOR—EO—MS (TEA) (1,000) | | | | | | | | 1 | | | | | | | |
| SOR—PO—TP (Na) (15,000) | | | | | | | | | | | | | | | |
| NPG—EO—DS (Na) (1,500) | | | | | | | | 3 | | | | | | | |
| Ethanol | 3 | 3 | 3 | 3 | 3 | 3 | 3 | 3 | | | | | | | |
| Water | Balance | Balance | Balance | Balance | Balance | Balance | Balance | Balance | | | | | | | |
| Detergency (number of plates) | 7 | 7 | 7 | 7 | 7 | 7 | 7 | 7 | | | | | | | |
| Foaming power (mm) | 90 | 91 | 92 | 90 | 90 | 91 | 90 | 90 | | | | | | | |
| Rinsing property (times) | 5 | 5 | 5 | 5 | 5 | 5 | 5 | 5 | | | | | | | |
| Feel to hands | | | | | | | | | | | | | | | |
| During use | +8 | +9 | +9 | +8 | +8 | +8 | +8 | +8 | | | | | | | |
| After use | +10 | +11 | +11 | +10 | +10 | +10 | +10 | +10 | | | | | | | |
| Ability to make hands rough | 4.7 | 4.8 | 4.8 | 4.8 | 4.7 | 4.6 | 4.7 | 4.7 | | | | | | | |

TABLE 3-continued

| Component | | | | Composition No. (weight percent) | | | | | | |
|---|---|---|---|---|---|---|---|---|---|---|
| EGL—EO—MS | (Na) | (700) | | | 0.5 | | | | | |
| GLY—PO—DS | (K) | (1,500) | | 2 | | | | 0.05 | | |
| GLY—PO—DP | (Na) | (1,500) | | | | 8 | | | 12 | |
| PGL—EO—TS | (Na) | (6,000) | | | | | | | | |
| PGL—PO—TP | (K) | (4,000) | | | | | | | | |
| PET—EO—MS | (TEA) | (2,000) | | | | | | | | |
| PET—PO—DP | (K) | (2,000) | | | | | | | | |
| SOR—EO—MS | (TEA) | (1,000) | | | | | | | | |
| SOR—PO—TP | (Na) | (15,000) | | | | | | | | 5 |
| NPG—EO—DS | (Na) | (1,500) | | 1 | | | | | | |
| Ethanol | | | | 3 | 3 | 3 | 3 | 3 | 3 | 3 |
| Water | | | | Balance | Balance | Balance | Balance | Balance | Balance | Balance |
| Detergency (number of plates) | | | | 7 | 6 | 7 | 4 | 3 | 3 | 2 |
| Foaming power (mm) | | | | 91 | 89 | 92 | 35 | 27 | 20 | 0 |
| Rinsing property (times) | | | | 5 | 6 | 5 | 8 | 9 | 9 | 9 |
| Feel to hands | | | | | | | | | | |
| During use | | | | +8 | +7 | +8 | +1 | +2 | +1 | ±0 |
| After use | | | | +10 | +9 | +10 | +1 | +1 | +1 | ±0 |
| Ability to make hands rough | | | | 4.7 | 4.6 | 4.8 | 3.0 | 2.9 | 3.1 | 2.5 |

EXAMPLE 9

The liquid detergent compositions specified in Table 4 were prepared using various alkyl glycosides and various polyhydric alcohol propylene oxide/ethylene oxide (PO/EO) adduct sulfate ester salts or phosphate ester salts. They were evaluated for detergency, foaming power, rinsing property, feel to hands and hand roughening effect. The results obtained are shown in Table 4.

In the comparative test for the feel to hands during use and after use, the composition No. 9 specified in Table 3 was used as the detergent A and the detergent compositions Nos. 16-28 (in Table 4) each was used as the detergent B.

The abbreviations in the table should be interpreted in the same manner as in Example 8. "PE" stands for "PO/EO adduct".

Thus, for instance, GLY-PE[0.5/0.5]-TS(Na)(200) stands for glycerol-PO/EO adduct (average molecular weight 200) trisulfate ester salt (sodium salt). The numerical value in the brackets following the abbreviation PE indicates the PO/EO mole ratio.

TABLE 4

| Component | | | | | Composition No. (weight percent) | | | | | | | |
|---|---|---|---|---|---|---|---|---|---|---|---|---|
| | | | | | Product of the Invention | | | | | | | |
| | | | | | 16 | 17 | 18 | 19 | 20 | 21 | 22 | 23 |
| Component (a) | | | | | | | | | | | | |
| General formula (I) | | | | | | | | | | | | |
| $R^1$ | $R^2$ | x | y | G | | | | | | | | |
| $C_9$-$C_{11}$ alkyl | — | 0 | 1.5 | Glucose residue | 23 | 23 | 23 | | | | 23 | 23 |
| $C_{10}$-$C_{13}$ alkyl | $C_2$ | 1 | 1.2 | Glucose residue | | | | 23 | 23 | 23 | | |
| Component (c) | | | | | | | | | | | | |
| GLY—PE [0.5/0.5]—TS | (Na) | (200) | | | | | | | | | | |
| GLY—PE [0.5/0.5]—TS | (Na) | (2,000) | | | 3 | | | | | | | 2 |
| GLY—PE [0.5/0.5]—TP | (Na) | (6,000) | | | | 3 | | | | | | 1 |
| GLY—PE [0.8/0.2]—TS | (Na) | (2,000) | | | | | 3 | | | | | |
| GLY—PE [0.2/0.8]—DS | (Na) | (1,500) | | | | | | 3 | | | | |
| TMP—PE [0.5/0.5]—TS | (Na) | (1,000) | | | | | | | 3 | | | |
| PET—PE [0.5/0.5]—TP | (Na) | (500) | | | | | | | | 3 | | |
| SOB—PE [0.5/0.5]—TS | (Na) | (2,000) | | | | | | | | | 3 | |
| Ethanol | | | | | 3 | 3 | 3 | 3 | 3 | 3 | 3 | 3 |
| Water | | | | | Balance | Balance | Balance | Balance | Balance | Balance | Balance | Balance |
| Detergency (number of plates) | | | | | 7 | 7 | 7 | 7 | 7 | 7 | 7 | 7 |
| Foaming power (mm) | | | | | 90 | 88 | 89 | 90 | 89 | 88 | 88 | 89 |
| Rinsing property (times) | | | | | 5 | 5 | 5 | 5 | 5 | 5 | 5 | 5 |
| Feel to hands | | | | | | | | | | | | |
| During use | | | | | +8 | +8 | +8 | +8 | +8 | +8 | +8 | +8 |
| After use | | | | | +9 | +9 | +9 | +9 | +9 | +9 | +9 | +9 |
| Ability to make hands rough | | | | | 4.6 | 4.6 | 4.7 | 4.6 | 4.6 | 4.7 | 4.6 | 4.6 |

| | | | | | Product of the Invention | | Comparative Product | | |
|---|---|---|---|---|---|---|---|---|---|
| | | | | | 24 | 25 | 26 | 27 | 28 |
| Component (a) | | | | | | | | | |
| General formula (I) | | | | | | | | | |
| $R^1$ | $R^2$ | x | y | G | | | | | |
| $C_9$-$C_{11}$ alkyl | — | 0 | 1.5 | Glucose residue | 23 | 23 | 23 | 23 | 23 |
| $C_{10}$-$C_{13}$ alkyl | $C_2$ | 1 | 1.2 | Glucose residue | | | | | |
| Component (c) | | | | | | | | | |
| GLY—PE [0.5/0.5]—TS | (Na) | (200) | | | | | 3 | | |
| GLY—PE [0.5/0.5]—TS | (Na) | (2,000) | | | | | | 0.05 | |
| GLY—PE [0.5/0.5]—TP | (Na) | (6,000) | | | | | | | |
| GLY—PE [0.8/0.2]—TS | (Na) | (2,000) | | | 0.5 | | | | |

TABLE 4-continued

| Component | Composition No. (weight percent) | | | | |
|---|---|---|---|---|---|
| GLY—PE [0.2/0.8]—DS (Na) (1,500) | 8 | | | | |
| TMP—PE [0.5/0.5]—TS (Na) (1,000) | | | | | 12 |
| PET—PE [0.5/0.5]—TP (Na) (500) | | | | | |
| SOB—PE [0.5/0.5]—TS (Na) (2,000) | | | | | |
| Ethanol | 3 | 3 | 3 | 3 | 3 |
| Water | Balance | Balance | Balance | Balance | Balance |
| Detergency (number of plates) | 6 | 7 | 4 | 3 | 3 |
| Foaming power (mm) | 88 | 90 | 33 | 24 | 18 |
| Rinsing property (times) | 6 | 5 | 8 | 9 | 9 |
| Feel to hands | | | | | |
| During use | +7 | +8 | +1 | +1 | +1 |
| After use | +8 | +9 | +1 | +1 | +1 |
| Ability to make hands rough | 4.5 | 4.7 | 2.9 | 2.8 | 2.5 |

EXAMPLE 10

A shampoo (for hair or body) was prepared according to the following formulation:

| | (% by weight) |
|---|---|
| Alkyl glycoside*[1] | 20 |
| Thickener (hydroxyethylcellulose) | 0.2 |
| GLY—PO—MS (1,500)*[2] | 2 |
| Cocofatty acid diethanolamide | 0.5 |
| Ethanol | 3 |
| Perfume | q.s. |
| Water | balance |
| | 100 |

(pH adjusted to 7.0)
*[1] In general formula (I), $x = 1$, $y = 1.5$, $R^1 = C_{10}-C_{13}$, $R^2 = C_2$, G = glucose residue.
*[2] For interpretation of the abbreviation, refer to Example 8.

EXAMPLE 11

A bathroom detergent composition was prepared according to the following formulation:

| | (% by weight) |
|---|---|
| Alkyl glycoside*[3] | 5 |
| PET—EO—MP (2,000)*[4] | 3 |
| Citric acid | 4 |
| Perfume | q.s. |
| Colorant | q.s. |
| Water | balance |
| | 100 |

(pH adjusted to 5.0)
*[3] In general formula (I), $x = 0$, $y = 2.3$, $R^1 = C_{10}-C_{14}$ (branched), G = glucose residue.
*[4] For interpretation of the abbreviation, refer to Example 8.

EXAMPLE 12

A liquid cleanser was prepared according to the following formulation:

| | (% by weight) |
|---|---|
| Alkyl glycoside*[5] | 4 |
| SOR—PE[0.5/0.5]—DS (2,000)*[6] | 3 |
| Abrasive (silica) | 40 |
| Perfume | q.s. |
| Preservative | q.s. |
| Water | balance |
| | 100 |

(pH adjusted to 7.5)
*[5] In general formula (I), $x = 2$, $y = 1.1$, $R^1 = C_9-C_{11}$, $R^2 = C_2$, G = glucose residue.
*[6] For interpretation of the abbreviation, refer to Example 8.

EXAMPLE 13

The compositions specified below in Table 5 were prepared and evaluated for detergency, foaming powder, rinsing property, feel to hands during use and after use, and hand roughening effect by the respective methods mentioned hereinabove. The results obtained are shown in Table 5.

In the comparative test for the feel to hands during use and after use, the composition for comparison (composition No. 17 in Table 5) was used as the detergent A and the detergent compositions Nos. 1-16 shown in Table 5 each was used as the detergent B.

TABLE 5

| Component | Composition No. (weight percent) | | | | | | | | |
|---|---|---|---|---|---|---|---|---|---|
| | Product of the Invention | | | | | | | | |
| | 1 | 2 | 3 | 4 | 5 | 6 | 7 | 8 | 9 |
| Component (a) | | | | | | | | | |
| Alkyl glycoside of general formula (I) ($x = 0$, G: glucose residue) | | | | | | | | | |
| $R^1$  $y$ | | | | | | | | | |
| $C_9-C_{11}$ alkyl  1.2 | 23 | 23 | 23 | 23 | | | | 23 | 23 |
| $C_{10}-C_{12}$ alkyl  1.8 | | | | | 23 | 23 | 23 | | |
| Component (d) | | | | | | | | | |
| $C_{11}H_{23}CONH(C_2H_4O)_{10}H$ | 3 | | | | 3 | | | 2 | 2 |
| $C_{11}H_{23}CONHCH_2CH_2N\begin{smallmatrix}CH_2CH_2OH\\CH_2COONa\end{smallmatrix}$ | | 3 | | | | | | 2 | |

TABLE 5-continued

| Component | Composition No. (weight percent) | | | | | | | | |
|---|---|---|---|---|---|---|---|---|---|
| $C_{11}H_{23}CON\begin{matrix}CH_2CH_2OH\\CH_2CH_2N\begin{matrix}CH_2COONa\\CH_2COONa\end{matrix}\end{matrix}$ | | 3 | | | 3 | | | 2 | |
| $C_{13}H_{27}CONHCH_2CH_2N\begin{matrix}CH_2CH_2OH\\CH_2COOH.TEA*^1\end{matrix}$ | | | 3 | | | 3 | | | |
| Component (b) | | | | | | | | | |
| PPG100*$^2$ (diol type*$^3$) | | | | | | | | | |
| PPG1000*$^2$ (diol type*$^3$) | 3 | 3 | 3 | 3 | | | | 2 | 2 |
| PPG2000*$^2$ (triol type*$^4$) | | | | | 3 | | | | |
| PPG5000*$^2$ (triol type*$^4$) | | | | | | | | | |
| Trimethylolpropane-EO adduct (1500*$^2$) | | | | | | 3 | | | |
| Sorbitol-PO adduct (3000*$^2$) | | | | | | | 3 | | |
| Water | Balance | Balance | Balance | Balance | Balance | Balance | Balance | Balance | Balance |
| Detergency (number of plates) | 8 | 8 | 8 | 8 | 8 | 8 | 8 | 8 | 8 |
| Foaming power (mm) | 95 | 95 | 96 | 96 | 94 | 94 | 93 | 95 | 96 |
| Rinsing property (times) | 5 | 5 | 5 | 5 | 5 | 5 | 5 | 5 | 5 |
| Feel to hands | | | | | | | | | |
| During use | +10 | +9 | +10 | +9 | +9 | +9 | +9 | +9 | +9 |
| After use | +10 | +10 | +10 | +10 | +10 | +10 | +10 | +10 | +10 |
| Ability to make hands rough | 4.7 | 4.7 | 4.8 | 4.7 | 4.7 | 4.7 | 4.8 | 4.7 | 4.8 |

| | Product of the Invention | | | | Comparative Product | | | |
|---|---|---|---|---|---|---|---|---|
| | 10 | 11 | 12 | 13 | 14 | 15 | 16 | 17 |
| Component (a) | | | | | | | | |
| Alkyl glycoside of general formula (I) (x = 0, G: glucose residue) | | | | | | | | |
| R$^1$   y | | | | | | | | |
| C$_9$-C$_{11}$ alkyl   1.2 | 23 | 23 | 23 | 23 | 23 | 23 | | 23 |
| C$_{10}$-C$_{12}$ alkyl   1.8 | | | | | | | 23 | |
| Component (d) | | | | | | | | |
| $C_{11}H_{23}CONH(C_2H_4O)_{10}H$ | | | | | 2 | | | |
| $C_{11}H_{23}CONHCH_2CH_2N\begin{matrix}CH_2CH_2OH\\CH_2COONa\end{matrix}$ | 2 | 2 | 3 | | | 3 | | 0.05 |
| $C_{11}H_{23}CON\begin{matrix}CH_2CH_2OH\\CH_2CH_2N\begin{matrix}CH_2COONa\\CH_2COONa\end{matrix}\end{matrix}$ | 2 | | | 3 | | | 3 | |
| $C_{13}H_{27}CONHCH_2CH_2N\begin{matrix}CH_2CH_2OH\\CH_2COOH.TEA*^1\end{matrix}$ | | 2 | | | | | | |
| Component (b) | | | | | | | | |
| PPG100*$^2$ (diol type*$^3$) | | | | | 2 | | | |
| PPG1000*$^2$ (diol type*$^3$) | 2 | 1 | 0.5 | | | | | |
| PPG2000*$^2$ (triol type*$^4$) | | | | 8 | | | | |
| PPG5000*$^2$ (triol type*$^4$) | | | | | | | 3 | |
| Trimethylolpropane-EO adduct (1500*$^2$) | | 1 | | | | | | |
| Sorbitol-PO adduct (3000*$^2$) | | | | | | | | 0.05 |
| Water | Balance | Balance | Balance | Balance | Balance | Balance | Balance | Balance |
| Detergency (number of plates) | 8 | 8 | 7 | 7 | 4 | 4 | 4 | 2 |
| Foaming power (mm) | 96 | 97 | 94 | 93 | 35 | 43 | 45 | 30 |
| Rinsing property (times) | 5 | 5 | 5 | 5 | 9 | 10 | 9 | 9 |
| Feel to hands | | | | | | | | |
| During use | +10 | +9 | +9 | +9 | +3 | +3 | +3 | ±0 |
| After use | +10 | +11 | +10 | +10 | +3 | +3 | +3 | ±0 |

TABLE 5-continued

| Component | Composition No. (weight percent) | | | | | | | |
|---|---|---|---|---|---|---|---|---|
| Ability to make hands rough | 4.8 | 4.8 | 4.7 | 4.6 | 3.3 | 2.8 | 3.2 | 3.8 |

Notes to Table 5:
*[1]TEA: triethanolamine
*[2]The numerical value indicates the average molecular weight of the compound.
*[3]Ethylene glycol-PO adduct
*[4]Glycerol-PO adduct

EXAMPLE 14

| Shampoo (for hair or body): | (% by weight) |
|---|---|
| Alkyl glycoside[1] | 15 |
| Amide type surfactant[2] | 3 |
| Polyoxyethylene ($\bar{p}$ = 2.5) lauryl ether sulfate triethanolamine salt | 5 |
| PG 1500 (diol type) | 2 |
| Ethanol | 3 |
| Cationized cellulose (Polymer JR400; produced by UCC Co., Ltd.) | 0.2 |
| Perfume | q.s. |
| Colorant | q.s. |
| Water | balance |
| | 100 |

(pH adjusted to 7.0)
[1]In general formula (I), x = 1, y = 1.6, $R^1$ = $C_{10}$-$C_{13}$, $R^2$ = $C_2$, G = glucose residue.

[2]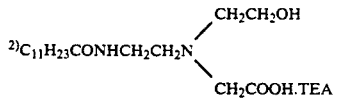

EXAMPLE 15

| Liquid light-duty detergent for clothing: | (% by weight) |
|---|---|
| Alkyl glycoside[3] | 20 |
| Amide type surfactant[4] | 3 |
| Polyoxyethylene (p = 4) alkyl ($C_{12}$-$C_{13}$) ether sulfate sodium salt | 2 |
| Glycerol-EO adduct (molecular weight 1,000) | 1 |
| Latex (average particle size 0.5 μm) | 0.5 |
| Ethanol | 5 |
| Perfume | q.s. |
| Colorant | q.s. |
| Water | balance |
| | 100 |

(pH adjusted to 7.5)
[3]In general formula (I), x = 0, y = 2.3, $R^1$ = $C_{10}$-$C_{14}$ (branched), G = glucose residue.
[4]$C_{13}H_{17}COHN(C_2H_4O)_6H$

EXAMPLE 16

| Bathroom detergent composition: | (% by weight) |
|---|---|
| Alkyl glycoside[5] | 5 |
| Amide type surfactant[6] | 2 |
| Pentaerythritol-EO adduct (molecular weight 1,500) | 3 |
| citric acid | 4 |
| Perfume | q.s. |
| Colorant | q.s. |
| Water | balance |
| | 100 |

(pH adjusted to 5.0)
[5]In general formula (I), x = 0, y = 1.5, $R^1$ = $C_9$-$C_{11}$, G = glucose residue.

[6]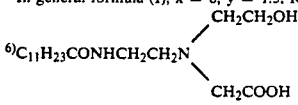

While the invention has been described in detail and with reference to specific examples thereof, it will be apparent to one skilled in the art that various changes and modifications can be made therein without departing from the spirit and scope thereof.

What is claimed is:

1. A detergent composition comprising the following components (a) and (b) in a (b)/(a) weight ratio within the range of 1/300 to ½:
   (a) an alkyl glycoside; and
   (b) a polyhydric alcohol-polyalkylene oxide adduct having an average molecular weight of 300 to 4,000, provided that when the polyhydric alcohol is ethylene glycol, the alkylene oxide is propylene oxide, and wherein component (b) is at least one selected from the group consisting of an ethylene glycol polypropylene oxide adduct, glycerol-polypropylene oxide adduct, sorbitol-polypropylene oxide adduct, pentaerythritol-polyproylene oxide adduct, glycerol-polyethylene oxide adduct, petnaerythritol-polyethylene oxide adduct and trimethylolpropane-polyethylene oxide adduct.

2. The detergent composition as claimed in claim 1, wherein the component (a) is an alkyl glycoside of formula (I):

$$R^1(OR^2)_xG_y \qquad (I)$$

wherein $R^1$ is a straight or branched alkyl or alkenyl group containing 8 to 18 carbon atoms or an alkylphenyl group in which the alkyl moiety may be straight or branched and contains 8 to 18 carbon atoms, $R^2$ is an alkylene group containing 2 to 4 carbon atoms, G is a residue derived from a reducing sugar containing 5 or 6 carbon atoms, x indicates a mean value and is a number equal to 0 to 5 and y indicates a mean value and is a number equal to 1 to 10.

3. The detergent composition as claimed in claim 1, wherein the component (b) is at least one selected from the group consisting of an ethylene glycolpolypropylene oxide adduct, glycerol-polypropylene oxide adduct, sorbitol-polypropylene oxide adduct, pentaerythritol-polypropylene oxide adduct, glycerol-polyethylene oxide adduct, pentaerythritol-polyethylene oxide adduct and trimethylolpropane-polyethylene oxide adduct.

4. A detergent composition comprising the following components (a) and (c) in a (c)/(a) weight ratio within the range of 1/300 to ½:
   (a) an alkyl glycoside;
   (c) a sulfate ester salt or a phosphate ester salt of a polyhydric alcohol-polyalkylene oxide adduct having an average molecular weight of 400 to 10,000, or mixtures thereof, wherein component (c) is a sulfate ester salt or a phosphate ester salt of an ethylene glycol-polyalkylene oxide adduct, glycerol-polyalkylene oxide adduct, pentaerythritolpolyalkylene oxide adduct, sorbitolpolyalkylene oxide adduct, neopentylglycol-polyalkylene oxide adduct, trimethylolpropane-polyalkylene oxide adduct or mixtures thereof.

5. The detergent composition as claimed in claim 4, wherein the component (a) is an alkyl glycoside of formula (I):

$$R^1(OR^2)_xG_y \qquad (I)$$

wherein $R^1$ is a straight or branched alkyl or alkenyl group containing 8 to 18 carbon atoms or an alkylphenyl group in which the alkyl moiety may be straight or branched and contains 8 to 18 carbon atoms, $R^2$ is an alkylene group containing 2 to 4 carbon atoms, G is a residue derived from a reducing sugar containing 5 or 6 carbon atoms, x indicates a mean value and is a number equal to 0 to 5 and y indicates a mean value and is a number equal to 1 to 10.

6. The detergent composition as claimed in claim 1, wherein said detergent composition further contains a nitrogen-containing surfactant as component (d) in a (d)/(a) weight ratio within the range of 1/300 to ½.

7. The detergent composition as claimed in claim 6, wherein said component (d) is a tertiary amine oxide, a carbobetaine, a sulfobetaine, a fatty acid alkanolamide, a polyethylene oxide adduct thereof or an amideamino acid type surfactant.

8. The detergent composition as claimed in claim 4, wherein said detergent composition further contains a nitrogen-containing surfactant as component (d) in a (d)/(a) weight ratio within the range of 1/300 to ½.

9. The detergent composition as claimed in claim 8, wherein said component (d) is a tertiary amine oxide, a carbobetaine, a sulfobetaine, a fatty acid alkanolamide, a polyethylene oxide adduct thereof or an amideamino acid type surfactant.

10. The detergent composition as claimed in claim 2, wherein $R^1$ is an alkyl or an alkenyl group which contains 10 to 14 carbon atoms.

11. The detergent composition as claimed in claim 2, wherein $R^2$ is an alkylene group containing 2 or 3 carbon atoms.

12. The detergent composition as claimed in claim 1, wherein component (a) is present in an amount of 1 to 60% by weight.

13. The detergent composition as claimed in claim 1, wherein component (b) is present in an amount of 0.1 to 10% by weight.

14. The detergent composition as claimed in claim 4, wherein component (c) is present in an amount of 0.1 to 10% by weight.

15. The detergent composition as claimed in claim 6, wherein component (d) is present in an amount of 0.1 to 10% by weight.

* * * * *